United States Patent [19]

Revici

[11] Patent Number: 4,962,129

[45] Date of Patent: Oct. 9, 1990

[54] TREATMENT OF SYMPTOMS OF NEOPLASTIC DISEASES WITHOUT TREATING THE DISEASES THEMSELVES

[75] Inventor: Emanuel Revici, New York, N.Y.

[73] Assignee: Elena Avram, New York, N.Y.

[21] Appl. No.: 834,689

[22] Filed: Feb. 28, 1986

Related U.S. Application Data

[63] Continuation-in-part of Ser. No. 806,142, Dec. 6, 1985, abandoned.

[51] Int. Cl.$^5$ .................. A61K 31/045; A61K 31/11; A61K 31/12; A61K 31/13
[52] U.S. Cl. .................................. 514/724; 514/625; 514/613; 514/693
[58] Field of Search .......................................... 514/724

[56] References Cited

U.S. PATENT DOCUMENTS 3,778,509  12/1973  Lewis ................................. 514/724
4,052,515  10/1977  McDermott et al. ............... 514/724

*Primary Examiner*—Jerome D. Goldberg
*Attorney, Agent, or Firm*—McAulay Fisher Nissen & Goldberg

[57] ABSTRACT

A method for treating the symptoms of a neoplastic disease without treating the disease itself which includes administering by injection an effective amount of a composition which includes the combination of two or more ketones, aldehydes, alcohols or amines having certain twin formation in a vegetable oil solution to a patient who is suffering from the symptoms of a neoplastic disease to alleviate at least some of such symptoms.

4 Claims, No Drawings

4,962,129

TREATMENT OF SYMPTOMS OF NEOPLASTIC DISEASES WITHOUT TREATING THE DISEASES THEMSELVES

CROSS REFERENCE TO RELATED APPLICATIONS

This application is a continuation-in-part of application Ser. No. 806,142, filed Dec. 6, 1985, now abandoned.

TECHNICAL FIELD

The present invention relates to compositions and methods for the treatment of symptoms of neoplastic diseases without treating the disease itself.

DETAILED DESCRIPTION OF THE INVENTION

I have found the existence of a dualism in the pathological conditions, corresponding to an anabolic-constructive or a catabolic-destructive imbalance. Symptoms and analytical data serve to recognize the type of imbalance present. Somnolence; hypothermia; constipation; polyuria; slow absorption of a skin wheel; blood eosinophilia; low serum potassium; low red cells sedimentation rates; no C reactive protein and urinary high surface tension; high pH; chloride and calcium excretion and low specific gravity characterize the anabolic imbalance. The opposite symptoms indicate a catabolic imbalance.

I found also the existence of a dualism in the activity of different agents. In general the ketones and aldehydes have an antianabolic action, while the positively charged alcohols and amines have an anticatabolic action. A method of treatment has resulted by using anabolic agents for the catabolic conditions and catabolic agents against anabolic conditions.

I have found that the presence in a molecule of a twin formation, that is, of two atoms with the same positive or negative electrical charge bound together, confers the molecule a high energetic activity. This is exerted especially upon the polar group near the twin formation.

I have found a special such activity for the molecules having two twin formations. The presence of a polar group bound to an odd numbered carbon of an aliphatic hydrocarbon having an odd number of carbons results in the presence of two twin formations. The same results have been found in aliphatic molecules having an even number of carbons with the polar group located on an even numbered carbon. The nature of the polar group determines the anabolic or catabolic character of the agent. The presence of a 3 or 5 ketone that is, of an oxygen atom bound to the carbons 3 or 5 of an aliphatic hydrocarbon having an odd number of carbons, or of a 2 or 4 ketone, where an oxygen atom is bound to the carbons 2 or 4 of an aliphatic hydrocarbon having an even number of carbons, confers to the compound a catabolic action, while a hydroxyl or amine group at the same position provides an anabolic character to the compound. The same catabolic action is found for other polar groups bound to the carbon atoms specified above, such as, for example the 3 or 5 aldehydes, and the 2 or 4 aldehydes.

Specific compounds which have been found to be useful include 3-pentanone; 3-heptanone; and 3 or 5 nonanone. These compounds, when two or more are used in combination, have provided very good action upon the symptoms of neoplastic disease without treating the diseases themselves. Propionic aldehyde in combination with a 3 or 5 ketone has also been found to be particularly effective. Combinations of 2-sec-butanone; 2-hexanone; 2 or 4 octanone; with any of the previously mentioned compounds which provide a catabolic action have been found effective. These compounds have been found effective in general for treatment of symptoms of any neoplastic diseases without treating the disease itself (i.e., whether such symptoms caused by either an anabolic or catabolic imbalance), but are even more effective for treating the symptoms caused solely by an anabolic imbalance.

Similarly, combinations of 3-pentanol; 3-heptanol; 3 or 5 nonanol; 3-penthylanone; 3-heptylanone; 3 or 5 nonylanone; 3-pentylamine; 3-heptylamine; and 3 and 5-nonylamines; 2-butanol; 2-hexanol; 2- or 4-octanol; 2-butylamine; 2-hexylamine; and 2 or 4 octylamine have a good action upon the symptoms of neoplastic diseases caused by a catabolic imbalance.

Especially favorable objective and subjective changes are found in suffering from the symptoms of neoplastic diseases without treating the diseases themselves when these compounds are administered. This indicates the important value of the combination of two agents each having the two twin formations described previously.

The use of two or more of these compounds, in combination, provides a much higher level of effectiveness for treatment of anabolic or catabolic symptoms of neoplastic diseases without treating the diseases themselves than the administration of a single agent. Preferred combinations are illustrated in the examples. The daily dosages vary according to the degree of the imbalance, but generally range from about ½ to 10 grams. No toxic effects have been encountered in patients which have received these compounds, even at the higher daily dosages.

All the formulations to be administered were prepared in dosages of approximately 600 mg, with the number of dosages to be taken per day depending upon the specific condition to be treated. 1 ml of a composition containing 60% of the compounds and 40% of a vegetable oil provides 600 mg of the active ingredient. Similarly, a 70% compounds/30% vegetable oil mixture, provides 700 mg for each 1 ml dose. The dosages can range from 1 ml given once a day to 4 ml administered twice a day. Preferably, such mixtures are administered by injection.

Solutions and suspensions of these agents in oils are preferred for administration by injection. While sesame oil, tung oil, and soybean oil are preferred, any vegetable oil can be used. It is also possible to use the oil extract from the seeds of a bixa or elana plant, and the term vegetable oil is used herein to include such extracts.

It is necessary to use at least 10% vegetable oil in the formulations to avoid causing pain to the patient upon administration. Thus, the oil is primarily used as a carrier. It is important that each administered dose contain at least 600 mg (60%) of the compounds having the twin formation. Thus, the overall dosage, per day, will vary from about 0.5 to 10 grams of compounds.

Injection at the site a tumor, or at another appropriate location (such as a painful area) is the preferred method of administration. Oral administration should be avoided because the liver tends to decrease the effectiveness of the composition.

An indication of neoplastic conditions is found especially in anabolic constructive imbalances, characterized by urines with a high surface tension, high pH and low specific gravity. The clinical results are indicated by a marked action upon the different manifestations especially pain, and the presence of tumors.

Predilectly the ketones and aldehydes are used to generally treat the symptoms of any neoplastic conditions without treating the conditions themselves, even independent of the nature of the imbalance present. As such, it represents a very important, and efficient new treatment for these diseases without treating the disease themselves.

The scheme of the treatment is the following: Urine analyses are made, preferably several times a day if the condition needs stronger treatment.

As basis agents, the ketones and/or aldehyde combinations are administered by injection. When an alkaline urine is found (i.e. a pH above 7), the higher dosages of these agents can be given. For a neutral urine (pH 6-7), the alcohol compounds are administered. For acid urine (pH below 6), the amine compounds are given.

With these compositions, especially good results, both subjective and objective, were obtained in the treatment of symptoms of various neoplastic diseases without treating the diseases themselves. One or more of the symptoms which may be alleviated include pain, weakness, anemia, loss of appetite and nausea.

EXAMPLES

The scope of the invention is further described in connection with the following example which is set forth for sole purpose of illustrating the preferred embodiments of the invention and which is not to be construed as limiting the scope of the invention in any manner.

The following formulations were prepared:

| Example 1. | | Example 2. | |
|---|---|---|---|
| 3-Pentanone | 30% | 3-Pentanone | 35% |
| 3-Heptanone | 30% | Propionic aldehyde | 35% |
| Sesame oil | 40% | Tung oil | 30% |
| Example 3. | | Example 4. | |
| 3-Pentanol | 30% | 3-Heptylamine | 30% |
| 3-Heptanol | 30% | 5-Heptylamine | 30% |
| Extract A | 20% | Extract B | 40% |
| Example 5. | | Example 6. | |
| 2-sec-Butanone | 40% | 2-Octanol | 33% |

-continued

| 2-Hexanone | 20% | 4-Octanol | 33% |
|---|---|---|---|
| Tung oil | 40% | Extract C | 34% |

Extract A is an oil extract of the seeds from a bixa plant; extract B is an oil extract of the seeds of an elana plant, while Extract C is a 50:50 mixture of Extracts A and B.

The compositions of Examples 1, 2, and 5 provide a catabolic action and thus are preferably used to treat an anabolic imbalance. Such catabolic agents can also be used to generally treat symptoms of neoplastic diseases when the type of imbalance cannot be determined. Conversely, the compositions of Examples 3, 4 and 6 provide an anabolic action, such that they are administered to patients exhibiting a catabolic imbalance.

These formulations were sterilized for injections. 2 ml injections of these compositions were given twice a day to a number of patients having various cancers, and all noted subjective improvements in the symptoms exhibited.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for alleviating the symptoms of a neoplastic disease without treating the disease itself which comprises administering by injection an effective amount of a composition comprising between about 60 and 90 weight percent of a mixture of substantially equal amounts of at least two different compounds selected from the group consisting of 3-pentanol, 3-heptanol, 3-nonanol and 5-nonanol; and between about 10 and 40 weight percent of a vegetable oil, said composition administered to a patient having symptoms of a neoplastic disease to alleviate at least one of said symptoms.

2. The method of claim 1 wherein the symptoms of said neoplastic disease includes pain, anemia, weakness, loss of appetite, and nausea.

3. The method of claim 1 wherein the effective amount is between 1 and 10 ml of the composition and is administered daily.

4. The method of claim 1 wherein the vegetable oil is tung oil, sesame oil, soybean oil, and oil extracted from the seeds of a bixa or elana plant, or mixtures thereof.

* * * * *